United States Patent

Krulevitch et al.

[11] Patent Number: 5,928,161
[45] Date of Patent: Jul. 27, 1999

[54] MICROBIOPSY/PRECISION CUTTING DEVICES

[75] Inventors: Peter A. Krulevitch, Pleasanton; Abraham P. Lee, Walnut Creek; M. Allen Northrup, Berkeley; William J. Benett, Livermore, all of Calif.

[73] Assignee: The Regents of the University of California, Oakland, Calif.

[21] Appl. No.: 08/887,780

[22] Filed: Jul. 3, 1997

[51] Int. Cl.⁶ .................................................. A61B 10/00
[52] U.S. Cl. .......................................... 600/564; 606/174
[58] Field of Search ................... 600/562, 564, 600/567, 570

[56] References Cited

U.S. PATENT DOCUMENTS 4,979,951  12/1990  Simpson ................................ 600/563

*Primary Examiner*—Robert L. Nasser
*Assistant Examiner*—Pamela L. Wingood
*Attorney, Agent, or Firm*—L. E. Carnahan

[57] ABSTRACT

Devices for performing tissue biopsy on a small scale (microbiopsy). By reducing the size of the biopsy tool and removing only a small amount of tissue or other material in a minimally invasive manner, the risks, costs, injury and patient discomfort associated with traditional biopsy procedures can be reduced. By using micromachining and precision machining capabilities, it is possible to fabricate small biopsy/cutting devices from silicon. These devices can be used in one of four ways 1) intravascularly, 2) extravascularly, 3) by vessel puncture, and 4) externally. Additionally, the devices may be used in precision surgical cutting.

18 Claims, 2 Drawing Sheets

MICROBIOPSY/PRECISION CUTTING DEVICES

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to biopsy tools, particularly to microbiopsy tools, and more particularly to gauging/scooping/scraping/ cutting microtools constructed of silicon and particularly applicable for performing microbiopsies, histological studies, and/or precision surgical cutting.

The science of preparing biopsied tissue samples for pathological study, known as histotechnology, requires skill and experience. In the past, to prepare tissue samples, biopsies were made using microtome blades which must be honed and stropped, and are capable of producing the required 5 µm thick slices only with great care. These biopsied tissue specimens were then embedded in paraffin wax, and then the specimens are sliced and mounted onto glass slides, all of which is a time consuming process. Furthermore, large quantities of chemicals are required to fix, dehydrate, and stain the tissue. Recent efforts have been directed to miniaturization and thus reducing the amount of chemicals required for sample studies. By reducing the size of the biopsy tool and removing only a small amount of tissue or other material in a minimally invasive manner, the risks, costs, injury and patient discomfort associated with traditional biopsy procedures can be reduced. Thus, there has been a need for microbiopy tools.

Using micromachining and precision capabilities, it is now possible to fabricate small devices for performing microbiopsies, thus the above-mentioned need has been fulfilled. It has been found that anisotropic etching of silicon results in extremely sharp edges, ideally suited for slicing soft tissues. In addition to their capability for performing microbiopsies, the tools of the present invention can be used for precision surgical cutting, for procedures in which micron scale portions of tissue must be removed.

SUMMARY OF THE INVENTION

An object of the present invention is to provide microtools for performing microbiopsies and precision surgical procedures.

A further object of the invention is to provide gauging/ scooping/ scraping/cutting microtools.

Another object of the invention is to provide microbiopsy/ precision cutting devices fabricated from silicon by a combination of silicon micromachining, conventional machining, precision machining and injection molding.

Another object of the invention is to provide microbiopsy/ precision cutting devices using anisotropic etching of silicon for producing extremely sharp edges, ideally suited for slicing soft tissues.

Other objects and advantages of the present invention will become apparent from the following description and accompanying drawings. The present invention is directed to microbiopsy/precision cutting devices for soft tissues or other material in a minimally invasive manner, thereby reducing the risks, costs, and possible injury to a patient, as well as, reducing patient discomfort associated with traditional biopsy procedures. The invention utilizes microdevices formed of silicon, for example, and by anisotropically etching of the silicon extremely sharp edges are formed. In addition to biopsies, the devices of this invention are applicable for precision surgical cutting and histological analysis. The embodiments of the invention enable slicing/gauging/scooping/scraping-type biopsy procedures. The devices of this invention are fabricated by various techniques including silicon micromachining, conventional machining, precision machining, and injection molding.

BRIEF DESCRIPTION OF THE DRAWINGS

The accompanying drawings, which are incorporated into and form a part of the disclosure illustrate embodiments of the invention and, together with the description, serve to explain the principles of the invention.

DETAILED DESCRIPTION OF THE INVENTION

The present invention involves microbiopsy/precision cutting devices for performing tissue biopsy on a small scale. The procedure can be performed in one of four ways: 1) intravascularly, to obtain samples of plaque, clot, or thrombus; 2) extravascularly, for biopsies of cancerous cells or tumors; 3) a device can be guided through the vasculature to the location of a tumor, for example, the vessel punctured, and a biopsy performed on externally accessible tissue, such as skin or bowel tissue. Once reaching the target location, the microbiopsy devices acquires tissue by one of three ways: 1) slicing, 2) gauging or scooping, or 3) tearing. Also, the devices may be utilized for precision surgical cutting for procedures, in which micron-scale portions of tissue must be removed. These devices are fabricated by a combination of silicon micromachining, conventional machining, precision machining, and injection molding. Also anisotropic etching of the silicon components results in extremely sharp edges, ideally suited for slicing soft tissues.

The size of the device can be altered to facilitate taking micro-scale tissue samples from difficult to reach areas, for example, during laparoscopic or endovascular surgery. Taking small tissue samples is also desirable because it limits patient trauma.

Figure 1:
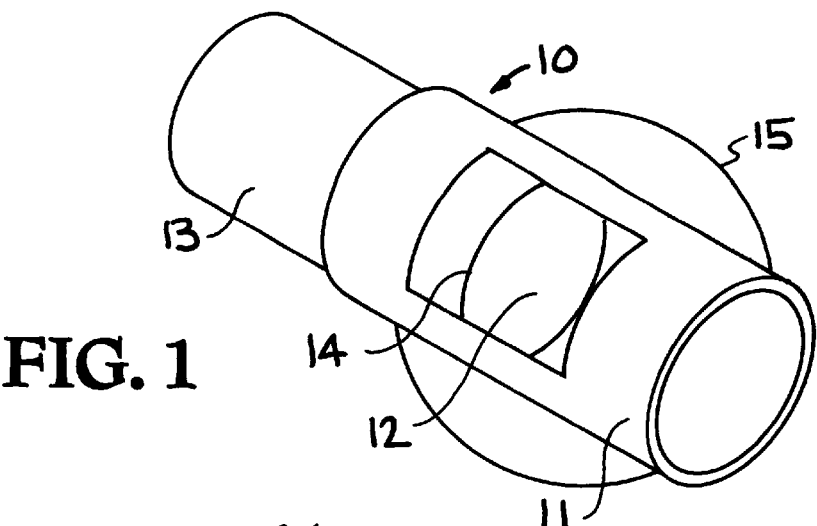
FIG. 1 is a perspective view of an embodiment of the invention using a cylinder within a cylinder.

Referring now to the drawings, FIG. 1 illustrates an embodiment of a device for slicing-type microbiopsies. As shown in FIG. 1, the device 10 comprises a first or outside cylinder 11, having a slot cut through the wall. forming a window 12, and a second or inside cylinder 13, which may be solid or hollow, having a sharp edge 14, and an actuator 15 such as a balloon as shown, or a spring, or wedge, attached to the outside cylinder 11 of a side opposite the window 12. The window 12 is pressed against the tissue to be biopsied using the actuator 15 to force tissue through the window 12. The inside cylinder 13 has an outer diameter (OD) slightly less than the inner diameter (ID) of outside cylinder 11. When the inside cylinder 13 is pushed through the outside cylinder 11, the sharp edge 14 causes slicing of the tissue which is pressed through the window 12, the tissue sample being retained within outside cylinder 11 or within inside cylinder 13 if hollow.

In the FIG. 1 embodiment the first or outside cylinder 11 has a closed end and the second or inside cylinder 13 is solid. If desired, both cylinders 11 and 13 may be hollow. By way of example, the cylinders 11 and 13 are preferably constructed of stainless steel or titanium, but may be constructed of other metals, plastic, silicon, ceramic, or glass, which are chemically compatible with the biopsy application. The outside cylinder 11 may have an OD of 0.2 to 2.0 mm, an ID of 0.15 to 1.9 mm, and window 12 may be rectangular, square, circular, etc., with an opening of 0.2 to 4.0 mm. The inside cylinder 13 may have an OD of 0.14 to 1.89 mm, slightly less than the ID of outside cylinder 11. The sharp leading edge 14 of cylinder 13 may be formed by machining operations, for example. The balloon actuator 15 may be constructed of a polymer such as polyurethane or urethane.

The FIG. 1 device can be modified to utilize square or rectangular members instead of cylindrical members, with the corners of the outer member being rounded to enable insertion of the device to a point of use.

Figure 2:
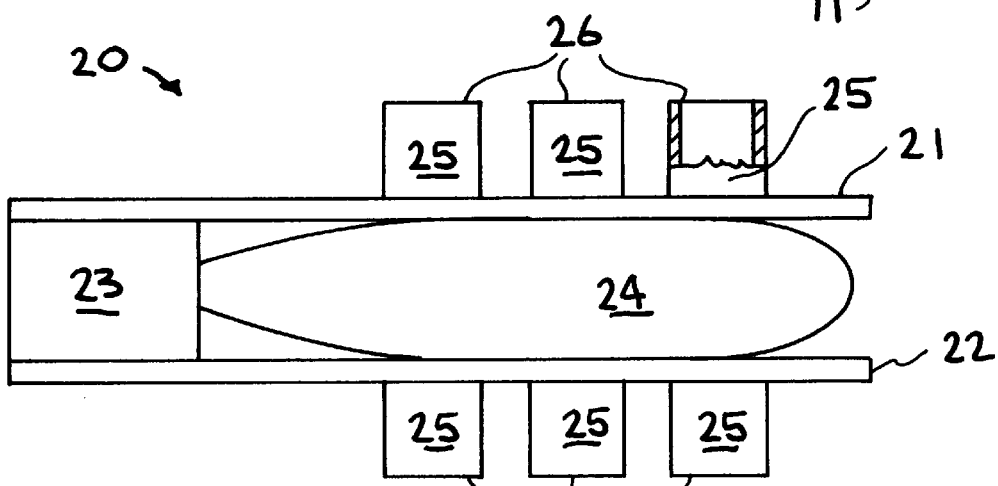
FIG. 2 is a view of another embodiment of the invention using silicon cantilevers to activate cutting tubes.
Figure 3:
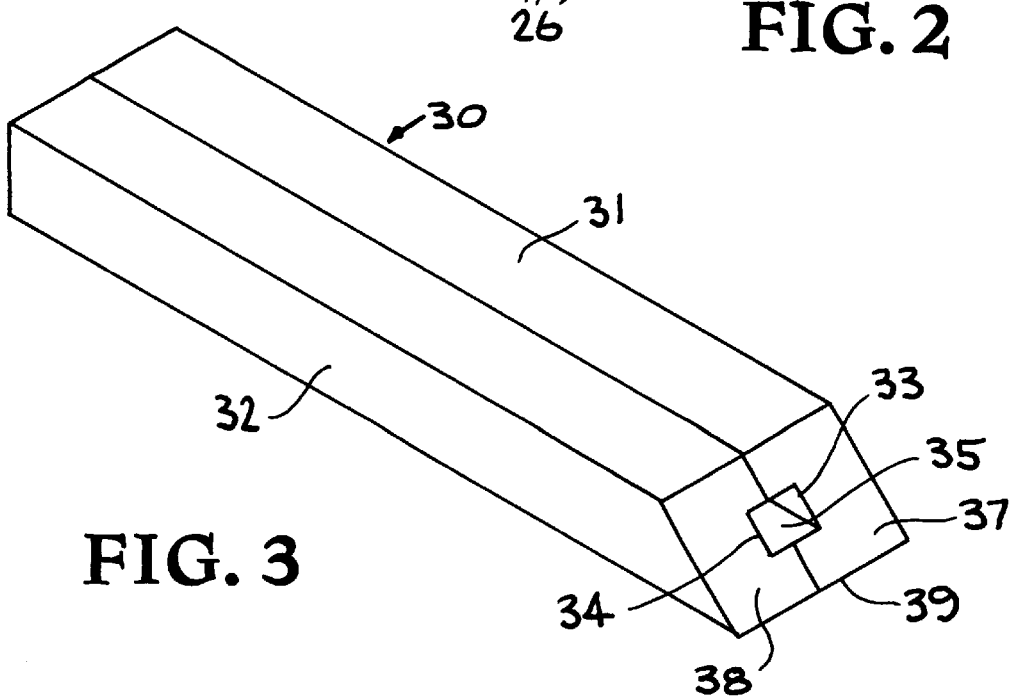
FIG. 3 illustrates another embodiment of the invention using a sharp leading edge and a hollow channel.
Figure 4:
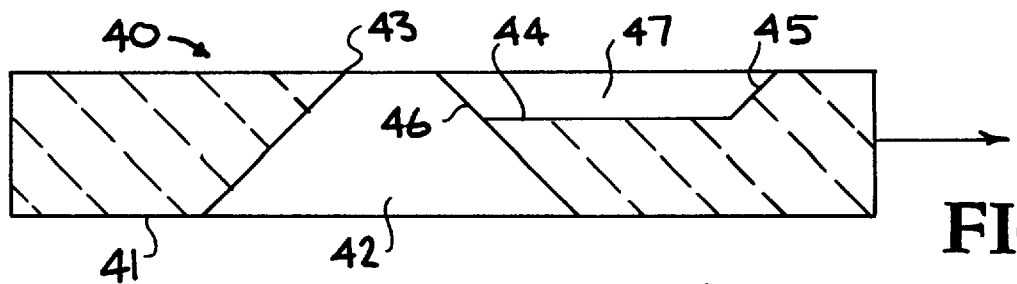
FIG. 4 illustrates in cross-section another embodiment of the invention using a sample trough and a collection pit below the cutter.

Gauging/scooping/scraping-type biopsy microtools are illustrated in FIGS. 2–4, wherein hollow micron scale members micromachined out of silicon can be used to take plug samples from within vessels, or puncture vessel walls to take tissue specimens from outside the vessels.

FIG. 2 shows a balloon-actuated cantilever device with sharpened silicon tubes for sampling tissue from the vessel wall, or puncturing the vessel to obtain a biopsy of extravascular tissue. While the FIG. 2 device is shown balloon-actuated, it could also be actuated with shape memory alloys, in bulk or film form, attached to one or both of the silicon cantilevers.

As shown in FIG. 2, the device indicated at 20 comprises a pair of cantilevers or arms 21 and 22 secured to a base member 23, and between which is located an actuating balloon 24. Cantilevers 21 and 22 are provided with a plurality (three shown) of cutting tubes or hollow members 25, which may include an outer pointed cylindrical edge, not shown. The cutting tubes are provided with sharp cutting edges 26. The cantilevers 21 and 22, base member 23 and cutting tubes 25 are preferably constructed of stainless steel or titanium, but may be composed of other suitable and compatible materials, including other metals, plastic, silicon, ceramic and glass, or constructed from a combination of these materials. If desired four cantilevers can be used, each extending from base member 23.

In operation, the device 20 is inserted into a vessel to a point where a biopsy is desired, and the actuating balloon 24 is inflated forcing cantilevers 21 and 22 outwardly, causing the cutting tubes 25 to puncture the vessel wall, the punctured tissue being retained in the tubes 25. Upon deflation of the balloon 24 the cutting tubes 25 are withdrawn, whereafter the device 20 can be withdrawn from the vessel with the biopsied tissue remaining in the cutting tubes 25. By way of example, the cantilevers 21 and 22 may have a length of 0.2 to 4.0 mm, width of 0.1 to 3.0 mm, and thickness of 0.1 to 1.0 mm, and separated by a distance of 0.1 to 2.0 mm. The cutting tubes 25 may be secured to the cantilevers by bonding, etc. and composed of stainless steel having an OD of 0.15 to 2.0 mm and ID of 0.1 to 1.9 mm, with a length of 0.1 to 3.0 mm. The actuating balloon 24 may be composed of a polymer such as polyurethane or urethane and connected to a gas, air, or fluid supply, not shown, for inflating/deflating of the balloon.

In FIG. 2, the cutting tubes 25 may be replaced with hollow cutting members of other configurations. For example, the cutting member could be a hollow square member composed of silicon with the edges 26 formed by anisotropic etching.

FIG. 3 illustrates a scooping-type biopsy device indicated at 30 comprising a pair of members 31 and 32 having respective cut-away sections 33 and 34 to form a hollow channel 35 when bonded together as indicated at 36. Member 31 and 32 include tapered ends 37 and 38 which when bonded together form a sharp or cutting leading edge 39. In operation, the device 30 is moved through a vessel or on a surface tissue such that sharp leading edge 39 cuts the tissue and the cut tissue is scooped into the hollow channel 35, where after the device is withdrawn with the biopsied material remaining in hollow channel 35.

By the way of example, the members 31 and 32 are constructed of silicon, each having a length of 0.5 to 4.0 mm, width of 0.4 to 2.0 mm, and thickness of 0.1 to 1 mm, with the cut-away sections 33 and 34 each having a width of 0.2 to 1 mm and depth of 0.05 to 0.75 mm, such that when combined the hollow channel 35 has an area of 0.1 to 0.75 mm. The tapered ends 37 and 38 may be at a angle of about 35° to 55° for silicon or 10°–60° for other materials. The member 31 and 32 may be bonded together by: silicon fusion bonding; gold-silicon eutectic bonding; or adhesive bonding. While silicon is preferred wherein the sharp leading edge is formed by anisotropic etching, the device 30 can be constructed of other materials such as metal or certain plastics capable of maintaining a sharp leading edge. The angle of the tapered ends 37 and 38 are 54.7° for {100} silicon or 35.3° for {110} silicon, and this angle is formed by anisotropic etching of the silicon.

Figure 5:
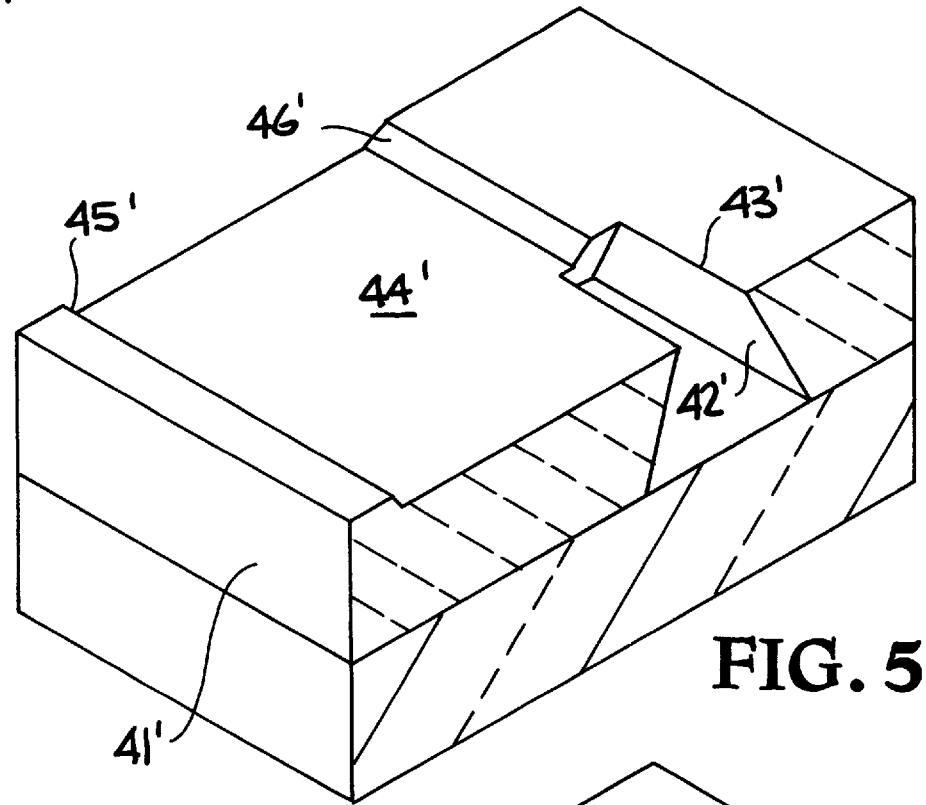
FIG. 5 is a cross-section view of another embodiment of the invention using a glass support and collection member.
Figure 6:
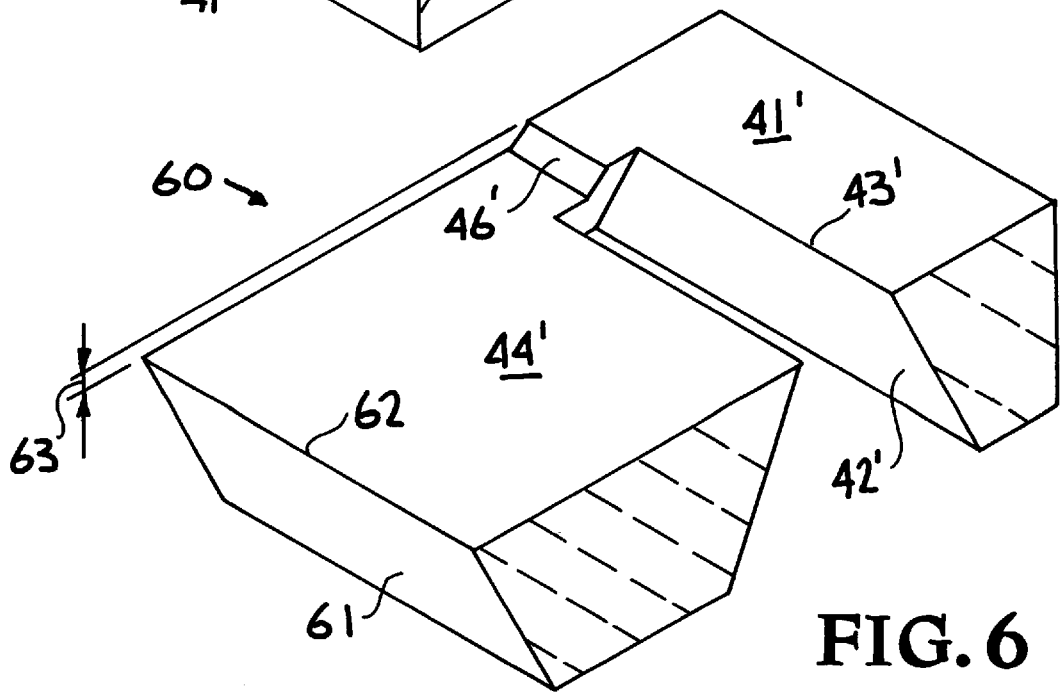
FIG. 6 is a cross-sectional view of a micro-cheese grater embodiment of the invention.

FIGS. 4, 5, and 6 illustrate cross-sectional views of a scraping-type biopsy device, similar to a conventional cheese-grater, and are bulk machined out of silicon, for example. The surface of a device is pressed against the tissue to be sampled, forcing some tissue into a tissue trough, where used, as shown in FIGS. 4 and 5, and as the device is pushed forward, the tissue in the trough is sliced by a sharp leading edge, and forced through an opening to the opposite side of the device, where it can be trapped, as described hereinafter with respect to FIG. 5. The FIG. 6 embodiment utilizes a precut edge rather than a trough. The sharp leading or cutting edge may be formed by anisotropic etching of the silicon.

As shown in FIG. 4 the biopsy device generally indicated at 40 comprises a body or member 41 having a tapered opening or collection pit 42 extending there through and defining a sharp leading or cutting edge 43. The opening 43 may define a slot extending partially across Body 41. Body 41 also includes a cut-away section 44 having a tapered surface 45 at one end and terminating as indicated at 46 in the tapered opening 42 to form a sample trough 47. The device 40 is positioned at a point where a biopsy is to be taken, either within a vessel or extravascularly, and the tissue to be sampled is pressed into the sample trough 47, whereafter the device 40 is moved in the direction of arrow 48 causing the tissue in the trough 47 to be cut by the sharp leading edge 43 and which drops into the opening or collection pit 42 of member 41. Opening 42 need not extend through member 41 if it is desired to retain the cut tissue therein, and in such a case a support member would be bonded to the lower surface of body 41.

By way of example, the member 41, preferably constructed of silicon has a length of 2 to 40 mm, width of 2 to 40 mm, and height (thickness) of 0.1 to 1.0 mm, with opening 42 tapering at an angle of 54.7° or 35.3° for silicon. The cut-away 44 may have a width of 1.0 to 35 mm, and length of 0.5 to 20 mm, with a depth determined by the desired thickness of the tissue sample to be taken (2 to 500 μm). The cut-away section 44 may extend fully or only partially across the upper surface of member 41 depending on the desired width of the sample trough 47. The body or member 41 may be constructed of other compatible materials that can be readily machined to form the opening 42, cut-away 44, and produce a sharp leading or cutting edge 43.

FIG. 5 is an extension of the FIG. 4 biopsy device with a glass-bottomed cavity to collect the tissue sample dropped through the opening or collection pit after being cut by the leading edge of the device. FIG. 5 is shown in partially cut-away to illustrate more clearly the sample opening or collection pit, the trough, and the cutting edge. Components similar to those of FIG. 4 will be utilized in FIG. 5. The device of FIG. 5 generally indicated at 50 comprises a block, body, or member 41', of silicon bonded or otherwise secured to a glass member 51, with tapered opening or collection pit 42' in member 41' abutting glass member 51. Note that the opening 42' defines a chamber having the appearance of a rectangular pyramid. Member 51 may also be constructed of silicon or compatible metal or plastic. Member 41' is provided with a cut-away section 44' having a tapered surface 45' and which terminates at 46' partially in opening 42' adjacent a cutting edge 43', to form a sample trough, as in the FIG. 4 device. In FIG. 5, the cutting edge 43' and opening 42' only extend across a portion of member 41' and cut-away section 44', but may extend substantially across the member 41' depending on the width of the tissue sample desired, but the opening must be terminated at one or both support ligaments, leaving sufficient material of member 41' to support itself (can not extend entirely across member 41') and prevent breakage of the device.

While not shown, the glass member 51 may be provided with analysis material containing slots in the upper surface thereof, whereby analysis of the biopsy sample dropped through opening 42' of member 41' can be carried out, thereby eliminating the need for sample handling. The depth of the sample trough or cut-away 44', as in FIG. 4, determines the thickness of the cut, and slices could be made from 2 to 500 μm thick tissue samples.

FIG. 6 is a modification of the devices illustrated in FIGS. 4 and 5, and differs by the elimination of the trough (44 or 44') and instead utilizes a pre-cut edge. Components of FIG. 6 similar to FIG. 5 are given corresponding reference numerals. As illustrated in FIG. 6, the device generally indicated at 60 comprises a block, body or member 41' of silicon, which if desired may be bonded to a glass member as in FIG. 5. The member 41' is provided with a tapered opening or collection pit 42' and a cut-away section 44' having a tapered surface 46' adjacent a thin slice or cutting edge 43' of opening 42'. As in FIG. 5, the opening 42' defines a rectangular pyramid chamber. The cut-away section 44' opposite the tapered surface 46' and a tapered end 61 of member 41' form a pre-cut edge 62. As in the embodiments of FIGS. 4 and 5 the slice thickness is determined by the depth of surface 46', as indicated at 63.

In addition to the embodiments illustrated in FIGS. 1–6, other microbiopsy/precision cutting devices have been considered. For example, a rotational type slicing device similar to currently available directional atherectomy devices, for taking specimens from the inner diameter of a vessel, wherein the cutters could be deployed by retracting a protective sheath, then rotated at the proximal end of the catheter to slice some tissue. Also, another technique for performing a microbiopsy involves tearing of the tissue, and an array of silicon microbarbs can be micromachined, whereby pressing these barbs into the tissue to be sampled and pulling away would tear off a biopsy sample and hold onto it. Also, microgrippers, such as described and claimed in copending U.S. application Ser. No. 08/446,146, filed May 22, 1995, entitled "Microfabricated Therapeutic Actuator Mechanisms", assigned to the same assignee, could be used as a microbiopsy tool by merely modifying the forward edges of one or both of the jaws to produce a sharp cutting edge.

It has thus been shown that the present invention provides microbiopsy/precision cutting devices for performing tissue biopsy on a small scale, and can be used intravascularly, extra-vascularly, puncturing the wall of a vessel and also obtaining samples through the vessel wall, and on externally accessible tissue. The devices can be fabricated from silicon, or other compatible material, using currently available machining and extruding techniques.

While particular embodiments of the invention have been illustrated and/or described, along with specific materials, parameters, etc., such are not intended to be limiting but have been set forth to exemplify and explain the principles of the invention. Modifications and changes may become apparent to those skilled in the art, and it is intended that the inventions be limited only by the scope of the appended claims.

The invention claimed is:

1. A microbiopsy/precision cutting device, including a solid movable member having an end defining a sharp leading edge, said sharp leading edge functioning to cut tissue when said end of said movable member is moved against tissue to be sampled, and means for retaining tissue cut by said leading edge, said movable member being constructed to move within said means for retaining tissue, said means for retaining tissue comprising a member having at least a hollow section through which said movable member moves, a window in said hollow section through which tissue to be sampled extends for cutting by said sharp leading edge, and additionally including means for causing tissue to extend through said window.

2. The device of claim 1, wherein at least said moveable member is constructed of material selected from the group consisting of silicon, metal, plastic, ceramic, and glass.

3. The device of claim 1, wherein said moveable member and said means for retaining tissue are of a cylindrical configuration.

4. A microbiopsy/precision cutting device, including a movable member having a sharp leading edge, said sharp leading edge functioning to cut tissue when moved against tissue to be sampled, means for retaining tissue cut by said sharp leading edge, said movable member comprising at least one hollow member secured to at least one cantilevered member, said sharp leading edge being located at an outer end of said at least one hollow member, said at least one hollow member comprising said means for retaining tissue cut by said sharp leading edge, and means for actuating said at least one cantilevered member.

5. The device of claim 4, wherein at least said plurality of hollow members and said plurality of cantilevered members are constructed of material selected from the group consisting of silicon, metal, plastic, ceramic, and glass.

6. The device of claim 4 wherein said moveable member comprises a plurality of tubes, said plurality of tubes being secured to a plurality of cantilevered members, said cantilevered members being spaced from one another, and means for activating said cantilevered members, said plurality of tubes comprising said means for retaining tissue cut by said sharp leading edge.

7. The device of claim 6, additionally including a base member separating said plurality of cantilever members and secured to one end thereof, and wherein said activating means comprises a balloon located between said cantilevered members.

8. A microbiopsy/precision cutting device, consisting of only a single member having a sharp edge, said sharp leading edge functioning to cut tissue when said member is moved against tissue to be sampled, and means in said member for retaining tissue cut by said sharp leading edge, said member including a tapered surface leading to said sharp leading edge, said member including a hollow channel therein, said hollow channel forming said means for retaining tissue cut by said leading edge.

9. The device of claim 8, wherein said movable member is composed of two members secured together, each of said two members including a cut-away section, which when secured together define said hollow channel.

10. The device of claim 9, wherein said two members are constructed of silicon and bonded together.

11. A microbiopsy/precision cutting device, including a movable member having a sharp leading edge, said sharp leading edge functioning to cut tissue when moved against tissue to be sampled, and means for retaining tissue cut by said sharp leading edge, said movable member including an opening therein, and a cutaway section, said sharp leading edge being located at one end of said opening, said cutaway section terminating adjacent said sharp leading edge.

12. The device of claim 11, wherein said opening is tapered.

13. The device of claim 12, wherein said cut-away section includes a tapered surface, and wherein said opening is tapered outwardly from said sharp leading edge.

14. The device of claim 11, wherein said opening comprises a tapered slot extending entirely through said movable member and extending traversely along a portion of said member.

15. The device of claim 11, wherein said cut-away section has a depth of 2–500 $\mu$m, thereby defining the thickness of a cut made by said sharp leading edge.

16. The device of claim 11, wherein said movable member is constructed of silicon.

17. The device of claim 11, wherein said opening extends through said movable member, and additionally including a member secured to said movable member which at least covers an end of said opening opposite said sharp leading edge.

18. The device of claim 17, wherein said movable member is constructed of silicon and wherein said member secured to said movable member is constructed of glass.

* * * * *